United States Patent
Caulfield et al.

(10) Patent No.: US 7,348,137 B2
(45) Date of Patent: *Mar. 25, 2008

(54) DETERMINATION OF TESTOSTERONE BY MASS SPECTROMETRY

(75) Inventors: Michael P. Caulfield, San Clemente, CA (US); Darren A Carns, Rancho Santa Margarita, CA (US); Richard E Reitz, San Clemente, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/247,409

(22) Filed: Oct. 11, 2005

(65) Prior Publication Data

US 2006/0040256 A1   Feb. 23, 2006

Related U.S. Application Data

(63) Continuation of application No. 10/726,919, filed on Dec. 2, 2003, now Pat. No. 6,977,143.

(60) Provisional application No. 60/501,255, filed on Sep. 8, 2003.

(51) Int. Cl.
*C12Q 1/00* (2006.01)
*G01N 33/00* (2006.01)

(52) U.S. Cl. .......................................... 435/4; 436/128

(58) Field of Classification Search ............ None
See application file for complete search history.

(56) References Cited

U.S. PATENT DOCUMENTS

| | | | |
|---|---|---|---|
| 5,772,874 A | 6/1998 | Quinn et al. | |
| 5,795,469 A | 8/1998 | Quinn et al. | |
| 5,919,368 A | 7/1999 | Quinn et al. | |
| 5,968,367 A | 10/1999 | Quinn et al. | |
| 6,107,623 A | 8/2000 | Bateman et al. | |
| 6,124,137 A | 9/2000 | Hutchens et al. | |
| 6,204,500 B1 | 3/2001 | Whitehouse et al. | |
| 6,268,144 B1 | 7/2001 | Koster | |
| 6,410,913 B1 | 6/2002 | Brekenfeld et al. | |
| 6,855,703 B1 * | 2/2005 | Hill et al. ................... | 514/170 |
| 2004/0235193 A1 | 11/2004 | Soldin | |

OTHER PUBLICATIONS

Williams et al. Electrospray Collision-induced Dissociation of Testosterone and Testosterone Hydroxy Analogs. J Mass Spectrom. 1999. vol. 34, pp. 206-216.*

Carignan et al., "High-performance liquid chromatographic analysis of estradiol valerate-testosterone enanthate in oily formulations" *J Chrom* 301(1):292-96 (1984).

Choi et al., "Rapid HPLC-Electrospray Tandem Mass Spectrometric Assay for Urinary Testosterone and Dihydrotestosterone Glucuronides from Patients with Benign Prostate Hyperplasia." Clin. Chem. 49: 322-5 (2003).

Choi et al., "Determination of Four Anabolic Steroid Metabolites by Gas Chromatogrophy/Mass Spectrometry with Negative Ion Chemical Ionization and Tandem Mass Spectrometry" *Rapid Commun. Mass Spectrom* 12, 1749-55 (1998).

Dorgan et al., "Measurement of steroid sex hormones in serum: a comparison of radioimmunoassay and mass spectrometry." Steroids 67: 151-8 (2002).

Draisci et al., Quantitation of anabolic hormones and their metabolites in bovine serum and urine by liquid chromatography—tandem mass spectrometry. Journal of Chromatography, 870: 511-522, 2000.

Furuta et al., "Simultaneous Measurements of Endogenous and Deuterium-Labelled Tracer Variants of Androstenedione and Testosterone by Capillary Gas Chromatography-Mass Spectrometry." *J Chrom, Biomed Appl* vol. 525: 15-23, (1990).

Giraudi et al., "Effect of Tracer Binding to Serum Proteins on the Reliability of a Direct Free Testosterone Assay." Steriods 52: 423-4 (1988).

Griffiths et al., Derivatisation for the characterization of neutral oxosteroids by electrospray and matrix-assisted laser desorption/ionization tandem mass spectrometry: the Girard P derivative. Rapid Communications in Mass Spectrometry, 17:924-935, 2003.

Lewis et al., DOT/FAA/AM-00/20 A Novel method for the determination of Sildenafil (Viagra®) and its metabolite (UK-103,320) in postmortem specimens using LC/MS/MS and LC/MS/MS/MS. National Technical Information Service, 2000, 3 cover pages and pp. 1-12.

Marcus and Durnford, "A Simple Enzyme-Linked Immunosorbent Assay for Testosterone." Steroids 46: 975-86 (1985).

Merchant and Weinberger, "Recent advancements in surface-enhanced laser desorption/ionization-time of flight-mass spectrometry." *Electrophoresis* 21: 1164-67 (2000).

Minut et al., "Urinary 5α-androstanediol and 5β-androstanediol measurement by gas chromatography after solid-phase extraction and high-performance liquid chromatography." *Int'l J Biol. Markers*, vol. 14(3); 154-59 (1999).

Ooi and Donnelly, "More on the Analog Free-Testosterone Assay." Clin. Chem. 45: 714-715 (1999).

Robb et al., "Atmospheric pressure photoionization: An ionization method for liquid chromatography-mass spectrometry." *Anal. Chem.* 72(15): 3653-3659 (2000).

(Continued)

Primary Examiner—Cecilia J. Tsang
Assistant Examiner—Marcela Cordero Garcia
(74) *Attorney, Agent, or Firm*—Foley & Lardner, LLP

(57) ABSTRACT

Provided are methods for determining the presence or amount of testosterone in a test sample, comprising ionizing all or a portion of the testosterone present in the sample to produce one or more testosterone ions that are detectable in a mass spectrometer. All or a portion of the testosterone present in the sample is ionized to produce one or more testosterone ions, which may be isolated and fragmented to produce precursor ions. A separately detectable internal testosterone standard can be provided in the sample. In a preferred embodiment, the reference is 2,2,4,6,6-$d_5$ testosterone.

50 Claims, No Drawings

OTHER PUBLICATIONS

Ropero-Miller et al., Simultaneous quantitation of opioids in blood by GC-EL-MS analysis following deproteination detautomerization of keto analytes, solid-phase extraction, and trimethylsilyl derivatization. Journal of Analytical Toxicology, 26: 524-528, 2002.

B. Starcevic, et al., "Liquid Chromatography—tandem Mass Spectrometry Assay For Human Serum Testosterone And Trideuterated Testosterone," *Journal of Chromatographyl B* 792:197-204 (2003).

Tiller et al., Drug quantitation on a benchtop liquid chromatography-tandem mass spectrometry system. Journal of Chromatography. 771: 119-125, 1997.

Winters et al., "The analog free testosterone assay: are the results in men clinically useful?" Clin. Chem. 44:2178-2182, (1998).

Wright et al., "Proteinchip surface enhanced laser desorption/ ionization (SELDI) mass spectrometry: a novel protein biochip technology for detection of prostate cancer biomarkers in complex protein mixtures." *Prostate Cancer and Prostatic Diseases* 2: 264-76 (1999).

Zimmer et al., "Comparison of turbulent-flow chromatography with automated solid-phase extraction in 96-well plates and liquid-liquid extraction used as plasma sample preparation techniques for liquid chromatography-tandem mass spectrometry." *J. Chromatogr. A* 854: 23-35 (1999).

* cited by examiner

DETERMINATION OF TESTOSTERONE BY MASS SPECTROMETRY

CROSS-REFERENCE TO RELATED PATENT APPLICATIONS

This application claims priority to U.S. Application Ser. No. 60/501,255, filed Sep. 8, 2003, and to U.S. application Ser. No. 10/726,919 filed Dec. 2, 2003, both of which are incorporated herein by reference in their entirety including all figures and tables.

FIELD OF THE INVENTION

The present invention relates to methods for analyzing testosterone and for detecting testosterone in samples by mass spectrometry.

BACKGROUND OF THE INVENTION

The following description of the background of the invention is provided simply as an aid in understanding the invention and is not admitted to describe or constitute prior art to the invention.

Testosterone (4 androsten 17β-ol-3-one) is a C19 steroid hormone with a molecular weight of 288.4 daltons. Testosterone is the major androgen in males and is controlled by luteinizing hormone (LH). LH is released from the anterior pituitary exerting the primary control on testosterone production, and acting directly on the Leydig cells in the testes, where testosterone is produced. Testosterone stimulates adult maturation of external genitalia and secondary sex organs, and the growth of beard, axillary and pubic hair. In addition, testosterone has anabolic effects leading to increased linear growth, nitrogen retention, and muscular development. Clinical evaluation of serum testosterone, along with serum LH, assists in evaluation of hypogonadal males. Major causes of lowered testosterone in males include hypogonadotropic hypogonadism, testicular failure, hyperprolactinemia, hypopituitarism, some types of liver and kidney diseases, and critical illness.

Testosterone levels are much lower in females compared to males. The major sources of testosterone in females are the ovaries, the adrenal glands, and the peripheral conversion of precursors, specifically the conversion of androstenedione to testosterone. In females, the normal levels of androgens may provide a substrate for estrogen production. Increased serum testosterone levels in females may be indicative of polycystic ovary syndrome and adrenal hyperplasia, among other conditions. The clinical manifestations of excess testosterone in females include infertility, hirsutism, amenorrhea, and obesity.

Testosterone strongly binds to plasma proteins such as sex hormone-binding globulin (SHBG) or testosterone-estradiol-binding globulin (TEBG). Testosterone also binds with low affinity to CBG (cortisol-binding globulins) and albumin. Less than 2.5% of testosterone circulates unbound to plasma proteins.

Numerous assays for testosterone are known to those of skill in the art. See, e.g., Marcus and Durnford, Steroids 46: 975-86 (1985); Giraudi et al., Steroids 52: 423-4 (1988); Ooi and Donnelly, Clin. Chem. 44: 2178-82 (1988); Dorgan et al., Steroids 67: 151-8 (2002); Choi et al., Clin. Chem. 49: 322-5 (2003).

SUMMARY OF THE INVENTION

In a first aspect, the present invention relates to methods for determining the presence or amount of testosterone in a test sample, comprising ionizing all or a portion of the testosterone present in the sample to produce one or more testosterone ions that are detectable in a mass spectrometer operating in positive ion mode, and detecting the ion(s) so produced. The presence or amount of one or more testosterone ions can be related to the presence or amount of testosterone in the original test sample.

Such methods may preferably comprise ionizing all or a portion of the testosterone present in the sample to produce one or more testosterone ions, isolating the testosterone ions by mass spectrometry to provide one or more precursor ions, fragmenting the precursor ions to provide one or more daughter ions that are detectable in a mass spectrometer operating in positive ion mode, and detecting the ion(s) so produced. The presence or amount of the testosterone daughter ion(s) can be related to the presence or amount of testosterone in the original test sample. Such methods are known in the art as "tandem mass spectrometry."

In preferred embodiments, a separately detectable internal testosterone standard is provided in the sample, the presence or amount of which is also determined in said sample. In these embodiments, all or a portion of both the endogenous testosterone and the internal standard present in the sample is ionized to produce a plurality of ions detectable in a mass spectrometer operating in positive ion mode, and one or more ions produced from each are detected by mass spectrometry.

In preferred embodiments, the testosterone ions detectable in a mass spectrometer include ions with a mass/charge ratio (m/z) of 289.1±0.5, 109.2±0.5, and/or 96.9±0.5, the latter two being fragments of the larger ion. In particularly preferred embodiments, the precursor ion has m/z of 289.1, while the fragment ions have an m/z of 109.2 and 96.9.

A preferred internal testosterone standard is 2,2,4,6,6,-$d_5$ testosterone. In preferred embodiments, the internal testosterone standard ions detectable in a mass spectrometer have a mass/charge ratio (m/z) of 294.1±0.5, 113.2±0.5 and/or 99.9±0.5. In particularly preferred embodiments, a precursor ion of the internal testosterone standard has an m/z of 294.1, and two fragment ions having an m/z of 113.2 and 99.9 are each detected.

In preferred embodiments, one may determine the specificity of testosterone determination by mass spectrometry by calculating a ratio of the daughter ions for that sample and comparing that ratio with that of a purified testosterone standard. The daughter ion ratio for purified testosterone is 1.43 (i.e. 109÷97) while the daughter ion ratio of the internal testosterone standard (2,2,4,6,6,-$d_5$ testosterone) is 1.07 (i.e. 113÷99). Under experimental conditions with multiple replicates, a median or mean and range derived from the standard deviation, coefficent of variation (CV) or percentage for each daughter ion ratio also can be calculated. In this way, the presence of an "unknown" compound (interfering substance) can be detected by either an increase or decrease in the observed daughter ion ratio.

In preferred embodiments, one may increase the signal to noise detection of testosterone (or the internal standard) by summing the signal of the detectable daughter ions for that sample. This has the effect of improving detection by increasing the signal and effectively reducing the background, thus improving the signal to noise ratio. In addition, one can quantitate the amount of testosterone in a sample by comparing the summed daughter ion signal of the unknown sample with a standard curve of summed daughter ion signals for known amounts of testosterone.

In certain embodiments, the testosterone present in a test sample can be purified prior to ionization. Numerous methods are known in the art to purify testosterone, including chromatography, particularly high performance liquid chromatography (HPLC), and thin layer chromatography (TLC); electrophoresis, including capillary electrophoresis; extraction methods, including ethyl acetate extraction, and methanol extraction; and affinity separations, including immunoaffinity separations; or any combination of the above.

Preferred embodiments utilize high turbulence liquid chromatography (HTLC), alone or in combination with one or more purification methods, to purify testosterone in samples. HTLC is a form of chromatography that utilizes turbulent flow of the material being assayed through the column packing as the basis for performing the separation. HTLC has been applied in the preparation of samples containing two unnamed drugs prior to analysis by mass spectrometry. See, e.g., Zimmer et al., *J. Chromatogr. A* 854: 23-35 (1999); see also, U.S. Pat. Nos. 5,968,367, 5,919,368, 5,795,469, and 5,772,874, which further explain HTLC and are each hereby incorporated by reference in their entirety including all charts and drawings. Persons of ordinary skill in the art understand "turbulent flow." When fluid flows slowly and smoothly, the flow is called "laminar flow." For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

Because the steps involved in these HTLC procedures can be linked in an automated fashion, the requirement for operator involvement during the purification of testosterone can be minimized. This can result in savings of time and costs, and eliminate the opportunity for operator error.

Purification in this context does not refer to removing all materials from the sample other than the analyte(s) of interest. Instead, purification refers to a procedure that enriches the amount of one or more analytes of interest relative to one or more other components of the sample. In preferred embodiments, purification can be used to remove one or more interfering substances, e.g., one or more substances that would interfere with detection of an analyte ion by mass spectrometry.

In various embodiments, the testosterone present in a test sample can be ionized by any method known to the skilled artisan. These methods include, but are not limited to, electron ionization, chemical ionization, fast atom bombardment, field desorption, and matrix-assisted laser desorption ionization ("MALDI"), surface enhanced laser desorption ionization ("SELDI"), photon ionization, electrospray, and inductively coupled plasma. The skilled artisan will understand that the choice of ionization method can be determined based on the analyte to be measured, type of sample, the type of detector, the choice of positive versus negative mode, etc.

Suitable test samples can include any liquid sample that can contain one or more testosterone. For example, samples obtained during the manufacture of synthetic testosterone can be analyzed to determine the composition and yield of the manufacturing process. In certain embodiments, a sample is a biological sample; that is, a sample obtained from any biological source, such as an animal, a cell culture, an organ culture, etc. Particularly preferred are samples obtained from a mammalian animal, such as a dog, cat, horse, etc. Particular preferred mammalian animals are primates, most preferably humans. Suitable samples include blood, plasma, serum, hair, muscle, urine, saliva, tear, cerebrospinal fluid, or other tissue sample. Such samples may be obtained, for example, from a patient; that is, a living person presenting themselves in a clinical setting for diagnosis, prognosis, or treatment of a disease or condition.

The mass spectrometer typically provides the user with an ion scan; that is, the relative abundance of each m/z over a given range (e.g., 100 to 900). The results of an analyte assay, that is, a mass spectrum, can be related to the amount of the analyte in the original sample by numerous methods known in the art. For example, given that sampling and analysis parameters are carefully controlled, the relative abundance of a given ion can be compared to a table that converts that relative abundance to an absolute amount of the original molecule. Alternatively, molecular standards can be run with the samples, and a standard curve constructed based on ions generated from those standards. Using such a standard curve, the relative abundance of a given ion can be converted back into an absolute amount of the original molecule. Numerous other methods for relating the presence or amount of an ion to the presence or amount of the original molecule are well known to those of ordinary skill in the art.

In other preferred embodiments, the purifying step involves (i) applying the sample to an HTLC extraction column, (ii) washing the HTLC extraction column under conditions whereby testosterone is retained by the column, (iii) eluting retained testosterone from the HTLC extraction column, (iv) applying the retained material to an analytical column, and (v) eluting purified testosterone from the analytical column. In preferred embodiments, the HTLC extraction column is a large particle C-18 extraction column, and the analytical column is a C-18 analytical column. The HTLC extraction column is preferably a large particle column.

By "large particle" column is meant a column containing an average particle diameter greater than about 35 µm. In the most preferred embodiment the column contains particles of about 50 µm in diameter, and the C-18 analytical column comprises particles of about 4 µm in diameter. As used in this context, the term "about" means±10%.

The term "analytical column" as used herein refers to a chromatography column having sufficient chromatographic "plates" to effect a separation of materials in a sample that elute from the column sufficient to allow a determination of the presence or amount of an analyte. Such columns are often distinguished from "extraction columns," which have the general purpose of separating or extracting retained material from non-retained materials in order to obtain a purified sample for further analysis.

In various embodiments, one of more steps of the methods can be performed in an inline, automated fashion. For example, in one embodiment steps (i)-(v) are performed in an inline, automated fashion. In another, the steps of ionization and detection are performed inline following steps (i)-(v). The term "inline, automated fashion" as used herein refers to steps performed without the need for operator intervention. For example, by careful selection of valves and connector plumbing, two or more chromatography columns can be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps.

In preferred embodiments, the purified testosterone is ionized by one or more of the following methods: electrospray ionization, chemical ionization, photon ionization, matrix-assisted laser desorption ionization (MALDI), and surface enhanced laser desorption ionization (SELDI). In the most preferred embodiment, the testosterone is ionized by electrospray ionization. In preferred embodiments, the testosterone ion is in a gaseous state and the inert collision gas is argon or nitrogen. The test sample is preferably obtained from a patient, for example, blood serum. In other embodiments the test sample can be blood plasma, or another liquid or biological fluid. In a most preferred embodiment the sample is de-proteinated prior to the ionization step by exposing the test sample to formic acid. The high turbulence liquid chromatography column most preferably contains a matrix of a C-12 carbon chain. In various embodiments, the mass spectroscopy is MS/MS/TOF mass spectroscopy, or MALDI/MS/MS/TOF mass spectroscopy, or SELDI/MS/MS/TOF mass spectroscopy.

In preferred embodiments, the presence or amount of the testosterone ion is related to the presence or amount of testosterone in the test sample by comparison to a reference 2,2,4,6,6-d5 testosterone sample.

The summary of the invention described above is non-limiting and other features and advantages of the invention will be apparent from the following detailed description of the invention, and from the claims.

DETAILED DESCRIPTION OF THE INVENTION

The present invention describes methods and compositions for unambiguously detecting testosterone in a test sample. The methods utilize liquid chromatography (LC), most preferably HTLC, to perform an initial purification of selected analytes, and combine this with unique methods of mass spectrometry (MS), thereby providing a high-throughput assay system for detecting and quantifying testosterone in a liquid sample. The preferred embodiments are particularly well suited for application in large clinical laboratories. Testosterone assays are provided that have enhanced specificity and are accomplished in less time and with less sample preparation than required in presently available testosterone assays. In various embodiments the methods of the invention accurately detect testosterone in samples where it is present in concentrations of less than 50 ng/dL, less than 25 ng/dL, less than 10 ng/dL, less than 5 ng/dL, and even less than 1 ng/dL. In various embodiments the concentration has a percent confidence of at least 90% or at least 93% or at least 95% or at least 97% or at least 98% or at least 99%. Persons of ordinary skill in the art understand statistical calculations and how to calculate a percent confidence for particular assays.

In one embodiment, the assay involves the combination of LC with mass spectrometry. In a preferred embodiment, the LC is HTLC. In another preferred embodiment, the mass spectrometry is tandem mass spectrometry (MS/MS).

Liquid chromatography (LC) and high-performance liquid chromatography (HPLC) rely on relatively slow, laminar flow technology. HPLC has been successfully applied to the separation of compounds in biological samples. But a significant amount of sample preparation is required prior to the separation and subsequent analysis with a mass spectrometer (MS), making this technique labor intensive. In addition, most HPLC systems do not utilize the mass spectrometer to its fullest potential, allowing only one HPLC system to be connected to a single MS instrument, resulting in lengthy time requirements for performing a large number of assays. High turbulence liquid chromatography (HTLC) methods that combine multiple separations in one procedure lessen the need for lengthy sample preparation and operate at a significantly greater speed. Such methods also achieve a separation performance superior to laminar flow (HPLC) chromatography. HTLC allows for direct injection of biological samples (plasma, urine, etc.). This is difficult to achieve in traditional forms of chromatography because denatured proteins and other biological debris quickly block the separation columns.

The terms "mass spectrometry" or "MS" as used herein refer to methods of filtering, detecting, and measuring ions based on their mass-to-charge ratio, or "m/z." In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., "Proteinchip surface enhanced laser desorption/ionization (SELDI) mass spectrometry: a novel protein biochip technology for detection of prostate cancer biomarkers in complex protein mixtures," *Prostate Cancer and Prostatic Diseases* 2: 264-76 (1999); and Merchant and Weinberger, "Recent advancements in surface-enhanced laser desorption/ionization-time of flight-mass spectrometry," *Electrophoresis* 21: 1164-67 (2000), each of which is hereby incorporated by reference in its entirety, including all tables, figures, and claims.

For example, in a "quadrupole" or "quadrupole ion trap" instrument, ions in an oscillating radio frequency field experience a force proportional to the DC potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

Moreover, one can often enhance the resolution of the MS technique by employing "tandem mass spectrometry," or "MS/MS." In this technique, a precursor ion or group of ions generated from a molecule (or molecules) of interest may be filtered in an MS instrument, and these precursor ions subsequently fragmented to yield one or more fragment ions that are then analyzed in a second MS procedure. By careful selection of precursor ions, only ions produced by certain analytes of interest are passed to the fragmentation chamber, where collision with atoms of an inert gas occurs to produce the fragment ions. Because both the precursor and fragment ions are produced in a reproducible fashion under a given set of ionization/fragmentation conditions, the MS/MS technique can provide an extremely powerful analytical tool. For example, the combination of filtration/fragmentation can be used to eliminate interfering substances, and can be particularly useful in complex samples, such as biological samples.

Additionally, recent advances in technology, such as matrix-assisted laser desorption ionization coupled with time-of-flight analyzers ("MALDI-TOF") permit the analysis of analytes at femtomole levels in very short ion pulses. Mass spectrometers that combine time-of-flight analyzers with tandem MS are also well known to the artisan. Additionally, multiple mass spectrometry steps can be combined in methods known as "MS/MS."

Ions can be produced using a variety of methods including, but not limited to, electron ionization, chemical ionization, fast atom bombardment, field desorption, and matrix-assisted laser desorption ionization ("MALDI"), surface enhanced laser desorption ionization ("SELDI"), photon ionization, electrospray ionization, and inductively coupled plasma.

The term "electron ionization" as used herein refers to methods in which one or more analytes of interest in a gaseous or vapor phase is/are interacted with a flow of electrons. Impact of the electrons with the analyte(s) produces analyte ions, which may then be subjected to a mass spectroscopy technique.

The term "chemical ionization" as used herein refers to methods in which a reagent gas (e.g. ammonia) is subjected to electron impact, and analyte ions are formed by the interaction of reagent gas ions and analyte molecules.

The term "fast atom bombardment" as used herein refers to methods in which a beam of high energy atoms (often Xe or Ar) impacts a non-volatile test sample, desorbing and ionizing molecules contained in the sample. Samples are dissolved in a viscous liquid matrix, such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

The term "field desorption" as used herein refers to methods in which a non-volatile test sample is placed on an ionization surface, and an intense electric field is used to generate analyte ions.

The term "matrix-assisted laser desorption ionization," or "MALDI" as used herein refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

The term "surface enhanced laser desorption ionization," or "SELDI" as used herein refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

The term "electrospray ionization," or "ESI," as used herein refers to methods in which a solution is passed along a short length of capillary tube, to the end of which is applied a high positive or negative electric potential. Solution reaching the end of the tube, is vaporized (nebulized) into a jet or spray of very small droplets of solution in solvent vapor. This mist of droplets flows through an evaporation chamber which is heated slightly to prevent condensation and to evaporate solvent. As the droplets get smaller the electrical surface charge density increases until such time that the natural repulsion between like charges causes ions as well as neutral molecules to be released.

The term "Atmospheric Pressure Chemical Ionization," or "APCI," as used herein refers to mass spectroscopy methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "Atmospheric Pressure Photoionization" ("APPI") as used herein refers to the form of mass spectroscopy where the mechanism for the photoionization of molecule M is photon absorption and electron ejection to form the molecular M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. Robb, D. B., Covey, T. R. and Bruins, A. P. (2000): See, e.g., Robb et al., Atmospheric pressure photoionization: An ionization method for liquid chromatography-mass spectrometry. *Anal. Chem.* 72(15): 3653-3659.

The term "inductively coupled plasma" as used herein refers to methods in which a sample is interacted with a partially ionized gas at a sufficiently high temperature to atomize and ionize most elements.

The term "ionization" and "ionizing" as used herein refers to the process of generating an analyte ion having a net electrical charge equal to one or more electron units. Negative ions are those ions having a net negative charge of one or more electron units, while positive ions are those ions having a net positive charge of one or more electron units.

The term "desorption" as used herein refers to the removal of an analyte from a surface and/or the entry of an analyte into a gaseous phase.

In those embodiments, such as MS/MS, where precursor ions are isolated for further fragmentation, collision-induced dissociation ("CID") is often used to generate the fragment ions for further detection. In CID, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

Sample Preparation for Mass Spectrometry

Numerous methods have been described to purify testosterone from samples prior to assay. For example, high performance liquid chromatography (HPLC) has been used to purify samples containing testosterone using C-18 column with an 8:2 methanol:water mixture at 1 ml/min. Mass spectrometry and gas chromatography has been used to analyze metabolites of anabolic steroids (See Choi et al., *Rapid Commun. Mass Spectrom* 12, 1749-55 (1998); Furuta et al., *J Chrom, Biomed Appl* (1990), Vol. 525: 15-23; Carignan et al., *J Chrom* 301(1):292-96 (1984); Minut et al., *Int'l J. Biol. Markers, Vol.* 14(3); 154-59 (1999)).

Recently, high turbulence liquid chromatography ("HTLC") has been applied for sample preparation of samples containing two unnamed drugs prior to analysis by mass spectrometry. See, e.g., Zimmer et al., *J. Chromatogr. A* 854: 23-35 (1999); see also, U.S. Pat. Nos. 5,968,367; 5,919,368; 5,795,469; and 5,772,874, each of which is hereby incorporated by reference in its entirety. Traditional HPLC analysis relies on column packings in which laminar flow of the sample through the column is the basis for separation of the analyte of interest from the test sample. The skilled artisan will understand that separation in such columns is a diffusional process. In contrast, it is believed that turbulent flow, such as that provided by HTLC columns and methods, may enhance the rate of mass transfer, improving the separation characteristics provided.

Additionally, the commercial availability of HTLC apparatuses that permit multiplexing of columns and direct integration with MS instruments makes such instruments particularly well suited to high-throughput applications.

Numerous column packings are available for chromatographic separation of samples, and selection of an appropriate separation protocol is an empirical process that depends on the sample characteristics, the analyte of interest, the interfering substances present and their characteristics, etc. For HTLC, polar, ion exchange (both cation and anion), hydrophobic interaction, phenyl, C-2, C-8, and C-18 columns are commercially available. During chromatography, the separation of materials is effected by variables such as choice of eluant (also known as a "mobile phase"), choice of gradient elution and the gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. The second mobile phase may be phased in gradually, usually under computer control directing the composition of mobile phase over time, or by an immediate change in the mobile phase. The retained materials may also be removed from the column by "backflushing" the column, or reversing the direction of flow of the mobile phase. This may be particularly convenient for material that is retained at the top of the column. Alternatively, an analyte may be purified by applying a sample to a column under mobile phase conditions where the analyte of interest elutes at a differential rate in comparison to one or more other materials. As discussed above, such procedures may enrich the amount of one or more analytes of interest relative to one or more other components of the sample.

The terms "phenyl," "C-2," "C-8," and "C-18" as used herein refer to functional groups present on a column packing material. For example, a phenyl column exposes the material flowing through the column to unsubstituted phenyl groups, while a C-18 column exposes the material flowing through the column to unsubstituted straight or branched chain 18-carbon alkyl groups.

The term "analytical column" as used herein refers to a chromatography column having sufficient chromatographic "plates" to effect a separation of materials in a sample that elute from a column sufficient to allow a determination of the presence or amount of an analyte without further purification on a chromatography column. However, further purification may occur by one or more other methods (e.g., mass spectrometry). Such columns are often distinguished from "extraction columns," which have the general purpose of separating or extracting retained material from non-retained materials.

In preferred embodiments, one or more of the purification and/or analysis steps can be performed in an "inline" fashion. The term "inline" as used herein refers to steps performed without further need for operator intervention. For example, by careful selection of valves and connector plumbing, two or more chromatography columns can be connected such that material is passed from one to the next without the need for additional manual steps. In preferred embodiments, the selection of valves and plumbing is controlled by a computer pre-programmed to perform the necessary steps. Most preferably, the chromatography system is also connected in such an in-line fashion to the detector system, e.g., an MS system. Thus, an operator may place a tray of samples in an autosampler, and the remaining operations are performed "in-line" under computer control, resulting in purification and analysis of all samples selected.

In contrast, the term "off-line" as used herein refers to a procedure requiring manual intervention of an operator after the test sample is loaded onto the first column. Thus, if samples are subjected to precipitation, and the supernatants are then manually loaded into an autosampler, the precipitation and loading steps are off-line from the subsequent steps.

Traditional HPLC analysis relies on the chemical interactions between sample components and column packings, where laminar flow of the sample through the column is the basis for separation of the analyte of interest from the test sample. The skilled artisan will understand that separation in such columns is a diffusional process. In contrast, it is believed that "turbulent flow," such as that provided by HTLC columns and methods, enhances the rate of mass transfer, thereby improving the separation characteristics provided by the separation system. HTLC columns separate components by means of high chromatographic flow rates through a packed column containing rigid particles. By employing high flow rates (e.g., 3-4 ml/min), turbulent flow occurs in the column that causes nearly complete interaction between the stationary phase and the analytes. An additional advantage of HTLC columns is that the macromolecular build-up associated with biological fluid matrices is avoided since the high molecular weight species are not retained under the turbulent flow conditions.

Numerous column packings are available for chromatographic separation of samples, and selection of an appropriate separation protocol is an empirical process that depends on the sample characteristics, the analyte of interest, the interfering substances present and their characteristics, etc. In preferred embodiments the HTLC columns have a media composition of styrene-divinylbenzene cross-linked copolymer with a median particle size of 60 μm (nominal) and a median particle pore size of 100 Å. In one embodiment the column dimensions are 1.0 mm ID×50 mm length, and the wetted parts of the apparatus are 316 stainless steel and styrene-divinylbenzene copolymer in a preferred embodiment. The preferred columns are silica-based HTLC columns configured to offer rapid processing. Various packing chemistries can be used depending on the needs (e.g., structure, polarity, and solubility of compounds being purified).

In various embodiments the columns are polar, ion exchange (both cation and anion), hydrophobic interaction, phenyl, C-2, C-8, C-18 columns, polar coating on porous polymer, and others are also commercially available. For purification of testosterone, it has been discovered that a column packed with a C-18 or C-8 matrix produces an advantageous separation. More preferably, the C-18 matrix contains bead sizes of about 50 um, trifunctional, at about 200 mg of beads per 3 ml. The total surface area is about 500 $m^2/gm$. Most preferably, the HTLC may be followed by HPLC on a C18 column with a porous spherical silica. During chromatography, the separation of materials is effected by variables such as choice of eluant (also known as a "mobile phase"), choice of gradient elution and the gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. As discussed above, such procedures may enrich the amount of one or more analytes of interest relative to one or more other components of the sample.

Daughter Ion Ratios for Specificity Determination

In preferred embodiments, one may determine the specificity of testosterone determination by mass spectrometry by calculating a ratio of the daughter ions for that sample and comparing that ratio with that of a purified testosterone standard. The daughter ion ratio for purified testosterone is 1.43 (i.e. 109÷97) while the daughter ion ratio of the internal testosterone standard (2,2,4,6,6,-$d_5$ testosterone) is 1.07 (i.e. 113÷99). Under experimental conditions with multiple replicates, a median or mean and range derived from standard deviation, CV or percentage for each daughter ion ratio also can be calculated. In this way, the presence of an "unknown" compound (interfering substance) can be detected by either an increase or decrease in the observed daughter ion ratio. Under experimental conditions with multiple replicates, a median and range and standard deviation for each daughter ion ratio also can be calculated. Automated rules can be programmed into the calculation/reporting program to look for these changes in ratios to help in identifying the presence of an "interfering" substance.

Daughter Ion Summation for Quantitation and Sensitivity

In preferred embodiments, one may increase the signal to noise detection of testosterone (or the internal standard) by summing the signal of the detectable daughter ions for that sample. This has the effect of improving detection by increasing the signal and effectively reducing the background, thus improving the signal to noise ratio. In addition, one can quantitate the amount of testosterone in a sample by comparing the summed daughter ion signal of the unknown sample with a standard curve of summed daughter ion signals for known amounts of testosterone. Automated rules can be programmed into the calculation/reporting program to sum the daughter ion values for each analysis.

The following examples serve to illustrate the present invention. These examples are in no way intended to limit the scope of the invention.

EXAMPLES

Example 1

Sample Preparation

A blood serum sample is collected from a human patient. The serum is first de-proteinated using a 10% formic acid solution or a 1% trichloroacetic acid solution (in methanol). The deproteination also acts to release testosterone from SHBG, albumin, and other binding proteins. In other embodiments proteins can be removed from the blood with other acids such as a with a solution of 1% trichloroacetic acid in methanol.

Sex hormone-binding globulin (SHBG) is a glycoprotein synthesized by the liver. SHBG's has a high affinity for testosterone that impacts bioavailable testosterone levels because hormone molecules are inactive until they are released and become free. SHBG binds up to 98 percent of the steroid hormones in the blood including 5a-dihydrotestosterone (DHT), testosterone, and androstenediol with particularly high affinity. The binding capacity of SHBG for testosterone is approximately 30,000 times greater than that of albumin.

To understand the stability of testosterone in samples, two levels of sample pool were subjected to the following conditions:

Freeze/Thaw: 1, 2, 3, 4, and 5 cycles.
Room Temperature: 0, 8, 24, 48, 96 and 168 hours.
Refrigerated (2-8° C.): 0, 1, 2, 4, 7, and 14 days.

Duplicate runs of samples were run on two separate days.

Table 1 summarizes the stability of testosterone in samples:

TABLE 1

| Sample Stability of Testosterone | |
|---|---|
| Condition | Stability |
| Refrigerated (0°-8° C.) | 7 Days |
| Room Temp (18-25° C.) | 4 Days |
| Freeze Thaw Cycles: | Up to 5 with no effect |

Example 2

Sample Analysis

This example provides a general description of a preferred embodiment of the methods for determining total testosterone in a sample.

During the HTLC procedure sample contaminants are eliminated through the turbulent flow regimen. As unbound and unwanted debris is swept through the extraction column at high velocity, the testosterone is captured and concentrated on the column. The extraction column is then back-flushed and the sample is loaded onto an analytical column. The HTLC system is then subjected to an elution gradient. The analytical column is in-line and allows for the chromatographic separation of the components of interest. A gradient/step function of 60% to 100% methanol is useful for enhancing this step.

Detection was accomplished using HTLC/MS/MS. The precursor ion, protonated molecule of interest, and any other ions of similar mass are isolated by the first MS (Q1). These ions enter a second chamber (Q2) where they collide with argon molecules. The collision-induced fragments differ for each molecular ion. Specific fragments produced only by the analyte ion are isolated by the final MS (Q3). The quantitation is based on the abundance of the final fragment ions. Mass transitions used for testosterone and the internal standard, 2,2,4,6,6-$d_5$ testosterone, are shown in Table 2.

TABLE 2

Testosterone and 2,2,4,6,6-$d_5$ Testosterone ion fragments

| Analyte | Precursor Ion | Fragment Ions |
| --- | --- | --- |
| Testosterone | 289.1 ± 0.5 m/z | 109.2 ± 0.5 m/z |
|  |  | 96.9 ± 0.5 m/z |
| 2,2,4,6,6-$d_5$ Testosterone | 294.1 ± 0.5 m/z | 113.2 ± 0.5 m/z |
|  |  | 99.9 ± 0.5 m/z |

After the removal of proteins from the serum, 90 μL of extracted sample was injected into the HTLC system using methanol and water in the mobile phase. The HTLC system is logically divided into two functions: 1) Solid phase extraction using a large particle size (e.g., 50 μm) packed column and 2) HPLC chromatography using a binary gradient and a 4 μm reverse phase analytical column. In this example a C-18 polymer column was used for extraction, which was endcapped, trifunctional, 500 m²/g, and had 50 μm particle size.

In the solid phase extraction mode of the HTLC system, the sample was first pumped through the extraction column at a high (greater than about 1.5 ml/min) flow rate using the HTLC loading pump. The high flow rate creates turbulence inside the extraction column. This turbulence ensures optimized binding of testosterone to the large particles in the column and the passage of residual protein and debris to waste.

After this loading step, the flow was reversed and the sample eluted off of the extraction column and transferred to the analytical HPLC column. The HPLC column was an all-purpose reverse phase column with a 4 μm, 80 Å silica gel. The gel particles were C-12 bonded phase with trimethyl chlorosiliane (TMS) endcapping suitable for moderately polar or non-polar analytes, acids, and bases over a broad pH range. Such HPLC columns are commercially available (e.g., MetaChem Polaris).

In the analytical mode of the HTLC, the sample was first loaded onto the analytical column. A binary gradient of from 60% to 100% methanol was used, resulting in the separation of testosterone from other analytes contained in the sample. The separated sample was then transferred to the MS/MS for quantitation.

Example 3

Detection and Quantitation of Testosterone by MS/MS

The flow of liquid solvent from the HTLC entered the heated nebulizer interface of the MS/MS analyzer. The solvent/analyte mixture was first converted to vapor in the heated tubing of the interface. The analytes, contained in the nebulized solvent, were ionized and a positive charge added by the corona discharge needle of the interface, which applies a large voltage to the nebulized solvent/analyte mixture. The ions passed through the orifice of the instrument and entered the first quadrapole. Quadrapoles 1 and 3 (Q1 and Q3) were the mass filters, allowing selection of ions based on their mass to charge ratio (m/z). Quadrapole 2 (Q2) was the collision cell, where ions were fragmented.

The first quadrapole of the MS/MS (Q1) selected for molecules with the mass to charge ratio of testosterone (289). Ions with this m/z passed to the collision chamber (Q2), while ions with any other m/z collided with the sides of the quadrapole and were destroyed. Ions entering Q2 collided with neutral gas molecules and fragment. This process is called Collisionally Activated Dissociation (CAD). The CAD gas used in this example was argon, resulting in the generation of different fragment ions than those obtained using nitrogen. The fragment ions generated were passed into quadrapole 3 (Q3), where the two fragment ions of testosterone to be measured (m/z 109.2±0.5 m/z & 96.9±0.5 m/z) were selected for, while other ions were screened out. The selected fragment ions were collected by the detector. The same process was carried out for an internal standard, which was a 5-deuterated testosterone molecule. Thus, the ion pairs measured were those shown in Table 2:

Selected MS/MS parameters were:

| | |
| --- | --- |
| Dwell time: | 250 msec |
| Res Q1: | 0.5 amu |
| Res Q2: | 0.7 |
| Curtain Gas: | 4 |
| CAD Gas: | 1.5 |
| NC Temp.: | 270° C. |
| Temp: | 350° C. |
| GS1: | 20 |
| GS2: | 0 |
| CE: | 20 |

As ions collide with the detector, they produce a pulse of electrons. The pulse was converted to a digital signal, which was counted to provide an ion count. The acquired data was relayed to the computer, which plotted counts of the ions collected vs. time. Heights of the peaks generated were computer-measured, response factors were generated from calibration material, and testosterone thereby quantitated in the sample.

The HTLC system can be operated with 1 to 4 columns in parallel. Given that a single assay requires about 4.75 minutes to traverse the column, by staggering the start time on each column, a 4-fold multiplexed system can inject four times as many test samples into the MS/MS instrument than with a single column. Thus, a set of 200 samples may be assayed for testosterone in 230 minutes using HTLC 4 fold muliplexing, as opposed to 2000 minutes by HPLC which allows only for a single column. Furthermore, following transfer of samples to the autosampler, no further operator handling of samples is required, as the HTLC may be computer-controlled to perform the subsequent purification and analysis steps in a fully in-line configuration.

Example 4

LOD (Limit of Detection)

Twenty one replicates of the zero standard (stripped serum; see below) were run to determine the reproducibility of the method. Statistical analysis was applied to determine the mean counts per second. The mean plus three standard deviations was extrapolated into the standard curve and viewed to determine the LOD. The LOD for the HTLC/MS/MS assay was 0.6 ng/dL. The results were as follows:

TABLE 3

LOD Determination

| | Stripped Serum |
|---|---|
| Mean (cps): | 836.3 |
| Standard Deviation (cps): | 140.2 |
| Mean + 3 SD (cps): | 1256.9 |
| LOD testosterone (ng/dL): | 0.6 |

Example 5

LOQ (Lower Limit of Quantitation)

The LOQ is the point where measurements become quantitatively meaningful and concentration where CV of the replicates is less than 20%. Standards for LOQ determination were prepared using an in-house pool of charcoal stripped serum. Biocell serum was mixed with Activated Charcoal, centrifuged, and the supernatant removed and saved. The newly prepared stripped serum was first run to check for any endogenous testosterone, of which none was detected. Five pools of different testosterone concentrations were prepared by spiking the stripped serum with testosterone standard in methanol. The levels of pools prepared were: 0.25 ng/dL, 0.5 ng/dL, 1.0 ng/dL, and 2.5 ng/dL. Each standard was run 5 times. The LOQ for the HTLC/MS/MS was determined to be 1 ng/dL from this study. The summarized results were as follows:

TABLE 4

LOQ Determination

| | 0.25 ng/dL | 0.5 ng/dL | 1.0 ng/dL | 2.5 ng/dL |
|---|---|---|---|---|
| Mean Testosterone Value (ng/dL) | 1.5 | 2 | 1.1 | 2.5 |
| Standard Deviation | 0.9 | 1.6 | 0.1 | 0.3 |
| % cv | 60% | 73% | 9% | 12% |

Example 6

Intra- and Inter-Assay Precision

Two levels of serum pools were run 20 times each within one run to obtain a measure of intra-assay precision. The results obtained are summarized as follows:

TABLE 5

Intra-assay precision

| | Low Pool | High Pool |
|---|---|---|
| Average Testosterone Value (ng/dL) | 21.7 | 142.8 |
| Standard Deviation | 2.8 | 16.1 |
| % cv | 13.1% | 11.3 |
| N: | 23 | 22 |

Three levels of serum pools were run 14 times each over 6 separate days (13 separate assays) to obtain a measure of inter-assay precision. The results obtained are summarized as follows:

TABLE 6

Inter-assay precision

| | Low Pool | Mid Pool | High Pool |
|---|---|---|---|
| Average Testosterone Value (pg/mL) | 283 | 2046 | 9148 |
| Standard Deviation | 37 | 123 | 1218 |
| % cv | 12.9% | 6.0% | 13.3% |
| n: | 32 | 32 | 32 |

Example 6

Accuracy

Total Testosterone results obtained from the HTLC/MS/MS assay were compared to those obtained using two other methodologies: Radioimmunoassay (RIA) and the Bayer Advia Centaur® automated platform.

Radioimmunoassay vs. HTLC/MS/MS:

140 Female samples were run on both RIA and HTLC/MS/MS Testosterone assays. The results obtained are summarized as follows in Table 6:

For 140 female adult samples:

| Female Samples RIA vs. HTLC/MS/MS | |
|---|---|
| $R^2$: | 0.573 |
| Slope | 0.840 |
| Y intercept | 6.4 |
| N: | 140 |

Bayer Advia Centaur vs. LC/MS/MS 243 adult samples (135 females and 108 males) were run on both Centaur and LC/MS/MS Testosterone assays. The results are summarized as follows in Tables 7, 8, and 9:

For all 243 samples (male and female):

| Female Samples Centaur vs. HTLC/MS/MS | |
|---|---|
| $R^2$: | 0.974 |
| Slope | 0.992 |
| Y intercept | −15.1 |
| N: | 243 |

For 135 female adult samples:

| Female Samples Centaur vs. HTLC/MS/MS | |
| --- | --- |
| $R^2$: | 0.437 |
| Slope | 0.529 |
| Y intercept | 4.7 |
| N: | 135 |

For 108 male adult samples:

| Female Samples Centaur vs. HTLC/MS/MS | |
| --- | --- |
| $R^2$: | 0.945 |
| Slope | 0.985 |
| Y intercept | −10.6 |
| N: | 108 |

Example 7

Linearity

A serial dilution consisting of 6 levels (Back calculation of the standard curve) was run in 10 separate assays. Recovery was calculated for each level. The assay was linear to 33333 pg/mL. The final results are summarized as follows:

TABLE 7

Assay Linearity

| Standard | 137 | 412 | 1235 | 3704 | 11111 | 33333 |
| --- | --- | --- | --- | --- | --- | --- |
| Average Testosterone Value (pg/mL) | 155 | 435 | 1186 | 3683 | 11082 | 33491 |
| Theoretical Gravimetric Value (pg/mL) | 137 | 412 | 1235 | 3704 | 11111 | 33333 |
| % Recovery | 113% | 106% | 96% | 99% | 100% | 101% |

Example 8

Assay Specificity

| Compound (Dose = 10 μg/dL) | Retention Time (mins.) (Analyte w/Interference) | Observed (ng/Dl) | % Interference |
| --- | --- | --- | --- |
| 5-AD-17β | 1.22 | 1500.0 | 15.0 |
| AD | N/D | — | 0.05 |
| 17-HP | N/D | — | 0.05 |
| PT | N/D | — | 0.05 |
| ESTRIOL | N/D | — | 0.05 |
| PT-ONE | 0.88 | 50.0 | 0.5 |
| 5-PT | 1.13 | 200.0 | 2.0 |
| CORTISOL | N/D | — | 0.05 |
| PD | N/D | — | 0.05 |
| 5α-THA | N/D | — | 0.05 |
| ETIO | N/D | — | 0.05 |
| 20α-DHE | N/D | — | 0.05 |
| 20β-DHE | N/D | — | 0.05 |
| 20α-DHF | N/D | — | 0.05 |
| 20β-DHF | N/D | — | 0.05 |
| ANDRO | N/D | — | 0.05 |
| THDOC | N/D | — | 0.05 |
| 5α-THB | N/D | — | 0.05 |
| THS | N/D | — | 0.05 |
| DHA | N/D | — | 0.05 |
| THE | N/D | — | 0.05 |
| THF | N/D | — | 0.05 |
| 5α-THF | N/D | — | 0.05 |
| A-CORTOLONE | N/D | — | 0.05 |
| B-CORTOL | N/D | — | 0.05 |
| CORTOLONE | N/D | — | 0.05 |
| α-CORTOL | N/D | — | 0.05 |
| THA | N/D | — | 0.05 |
| THB | N/D | — | 0.05 |
| 5α-THB | N/D | — | 0.05 |
| METHYLTESTO | N/D | — | 0.05 |

Example 9

Atmospheric Pressure Photoionization

This example describes an embodiment utilizing atmospheric pressure photoionization mass spectroscopy (APPI) in the present invention. As the information that follows indicates, APPI is a robust and sensitive triple quad MS system. The system offers improved ion transfer optics to enhance stability and sensitivity. An APPI system can be used either by itself or in combination with an APCI or API source.

The procedure is similar to that described in Example 2, but utilizes an APPI system, e.g. the Finnigan TSQ Quantum Discovery™ (ThermoFinnigan, San Jose, Calif.) or equivalent to assay for testosterone. This system is a robust and sensitive triple quadrupole mass spectrometry using photoionization. The assay offers enhanced specificity and reduced run-time and sample preparation. To this end two systems have been combined: HTLC and Tandem Mass Spectroscopy (e.g., the ThermoFinnigan system). Blood serum was used as the test sample for the assays described in this example, however, plasma samples are also acceptable. The mass transitions used where those in Table 2.

Various parameters of the assay were investigated. The limit of detection (LOD) is the point at which a measured value is larger than the uncertainty associated with it and is defined arbitrarily as 3 standard deviations (SD) from zero concentration. 21 replicates of the zero standard were analyzed to determine the mean counts per second of the twenty-one replicates and 3 SD was added. The mean+3 SD was extrapolated back into the standard curve and used to determine the LOD. The LOD for the assay was determined to be 0.6 ng/dL.

The lower limit of quantitation (LOQ) is the point where measurements become quantitatively meaningful and is set at the concentration where the CV of the replicates is <20%. Four low concentration pools were analyzed and the results statistically analyzed to determine the mean, standard deviation, and coefficient of variation. The LOQ for the assay was determined to be 1.0 ng/dL.

Intra-assay variation was measured to determine the precision of a sample value within an assay. The coefficient of variation (CV) for 20 replicates of a sample was determined and the precision was found to be acceptable (≦15% CV). Two sample pools were used to evaluate the intra-assay variation, a low concentration pool and a medium concentration pool. The low concentration pool (16-27 ng/dl) gave a CV of 13.1% with mean concentration of 21.7 ng/dL, and the medium pool (131-189 ng/dl) gave a CV of 11.3% with a mean of 142.8 ng/dL.

The inter-assay variation of a sample value was evaluated using a CV of <20% as acceptable. Three sample pools were analyzed in multiple assays. The low concentration pool (15-21 ng/dl) was found to have a CV of 11.5% with a mean concentration of 18.3 ng/dL.

Sample recovery was analyzed using two patient samples of different concentrations. These samples were diluted with mobile phase (1:1, 1:2, 1:4, 1:8). Sample #1 had 24.5 ng/dl and was diluted in the stated ratios into #2, which had a concentration of 312.7 ng/dl. Sample #3 had a concentration of 20.5 ng/dl and was diluted at the stated ratios into Sample #4, which had a concentration of 293.0 ng/dl. The samples were analyzed in singlet and the observed values (y) were compared to the expected values (x). Linear regression of the combined data showed that the mean percent recovery for all analytes was 103% for the two sets. The mean recovery was 99%.

The correlation of the assay was analyzed by assaying 49 serum samples for testosterone according to the APPI method against two commonly accepted testosterone assays—the testosterone radioimmunoassay and the ADVIA CENTAUR® assay (Bayer Diagnostics, Tarrytown, N.Y.). Linear regression analysis was performed on the combined data showing $y=0.87x+15.67$ with a $r^2$ of 0.95.

The contents of the articles, patents, and patent applications, and all other documents' and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A method for determining the presence or amount of testosterone in a test sample comprising,
    (a) purifying testosterone from the test sample by turbulent flow chromatography;
    (b) ionizing the purified testosterone to produce one or more testosterone ions detectable by a mass spectrometer having a mass/charge ratio selected from the group consisting of 289.1±0.5, 109.2±0.5, and 96.9±0.5; and
    (c) detecting the presence or amount of the testosterone ion(s) by a mass spectrometer, wherein the presence or amount of the testosterone ion(s) is related to the presence or amount of testosterone in the test sample, wherein said ionizing and detecting utilize tandem mass spectrometry/time-of-flight (MS/MS/TOF) spectroscopy.

2. The method of claim 1 wherein the ionizing of step (b) comprises,
    ionizing said testosterone from said sample to provide a precursor ion having a mass/charge ratio (m/z) of about 289.1±0.5;
    isolating the precursor ion by mass spectroscopy; and
    effecting a collision between the isolated precursor ion and an inert collision gas to produce one or more testosterone ions detectable by mass spectrometry having a mass/charge ratio selected from the group consisting of 109.2±0.5, and 96.9±0.5.

3. The method of claim 1, wherein the purifying step comprises:
    (i) applying the sample to a high turbulence liquid chromatography (HTLC) extraction column;
    (ii) washing the HTLC extraction column under conditions whereby testosterone is retained by the column;
    (iii) eluting retained testosterone from the HTLC extraction column;
    (iv) applying the retained material to an analytical column; and
    (v) eluting purified testosterone from the analytical column.

4. The method of claim 3, wherein steps (i)-(v) are performed in an in-line automated fashion.

5. The method of claim 3, wherein steps (a) and (b) are performed in an in-line automated fashion with steps (i)-(v).

6. The method of claim 1 wherein the ionization in step (b) is performed by a method selected from the group consisting of chemical ionization, photon ionization, and surface enhanced laser desorption ionization (SELDI).

7. The method of claim 1 wherein the ionization in step (b) is performed by atmospheric pressure photoionization (APPI).

8. The method of claim 1 wherein the test sample is obtained from a human.

9. The method of claim 1 wherein the test sample is blood, serum, plasma, or urine.

10. The method of claim 9 wherein the test sample is deproteinated prior to the ionization step.

11. The method of claim 1 wherein the presence or amount of the testosterone ion is related to the presence or amount of testosterone in the test sample by comparison to a reference sample.

12. The method of claim 11, wherein the reference sample is 2,2,4,6,6,-d5 testosterone.

13. The method of claim 12, wherein said reference sample is detected by ionizing said reference to produce one or more ions detectable by mass spectrometry having a mass/charge ratio selected from the group consisting of 294.1±0.5, 113.2±0.5, and 99.9±0.5.

14. The method of claim 13 wherein said ionizing comprises generating a precursor ion having a mass/charge ratio (m/z) of about 294.1±0.5;
isolating the precursor ion by mass spectroscopy; and
effecting a collision between the isolated precursor ion and an inert collision gas to produce one or more daughter ions detectable by mass spectrometry having a mass/charge ratio selected from the group consisting of 113.2±0.5, and 99.9±0.5.

15. The method of claim 1 further comprising determining the specificity of testosterone detection by calculating a ratio of the daughter ions for the sample and comparing that ratio with a daughter ion ratio for a purified sample of testosterone.

16. The method of claim 1 wherein detecting the presence or amount of the testosterone ion(s) by mass spectrometry involves combining the signal for ion 109.2±0.5 with the signal for ion 96.9±0.5 to obtained a summed daughter ion signal.

17. The method of claim 16 wherein the amount of testosterone is detected by comparing the summed daughter ion signal with a standard curve of summed daughter ion signals for known amounts of testosterone.

18. The method of claim 13 wherein detecting the presence or amount of the reference testosterone ion(s) by mass spectrometry involves combining the signal for ion 113.2±0.5, with the signal for ion and 99.9±0.5 to obtain a summed daughter ion signal.

19. A method for determining the presence or amount of testosterone in a test sample comprising,
(a) purifying testosterone from the test sample by turbulent flow chromatography;
(b) ionizing the purified testosterone by surface enhanced laser desorption ionization (SELDI) to produce one or more testosterone ions detectable by a mass spectrometer having a mass/charge ratio selected from the group consisting of 289.1±0.5, 109.2±0.5, and 96.9±0.5; and
(c) detecting the presence or amount of the testosterone ion(s) by a mass spectrometer, wherein the presence or amount of the testosterone ion(s) is related to the presence or amount of testosterone in the test sample, wherein said ionizing and detecting utilize tandem mass spectrometry/time-of-flight (MS/MS/TOF) spectroscopy.

20. The method of claim 19 wherein the ionizing of step (b) comprises,
ionizing said testosterone from said sample to provide a precursor ion having a mass/charge ratio (m/z) of about 289.1±0.5;
isolating the precursor ion by mass spectroscopy; and
effecting a collision between the isolated precursor ion and an inert collision gas to produce one or more testosterone ions detectable by mass spectrometry having a mass/charge ratio selected from the group consisting of 109.2±0.5, and 96.9±0.5.

21. The method of claim 19, wherein the purifying step comprises:
(i) applying the sample to a high turbulence liquid chromatography (HTLC) extraction column;
(ii) washing the HTLC extraction column under conditions whereby testosterone is retained by the column;
(iii) eluting retained testosterone from the HTLC extraction column;
(iv) applying the retained material to an analytical column; and
(v) eluting purified testosterone from the analytical column.

22. The method of claim 21, wherein steps (i)-(v) are performed in an in-line automated fashion.

23. The method of claim 21, wherein steps (a) and (b) are performed in an in-line automated fashion with steps (i)-(v).

24. The method of claim 19 wherein the test sample is obtained from a human.

25. The method of claim 19 wherein the test sample is blood, serum, plasma, or urine.

26. The method of claim 25 wherein the test sample is deproteinated prior to the ionization step.

27. The method of claim 19 wherein the presence or amount of the testosterone ion is related to the presence or amount of testosterone in the test sample by comparison to a reference sample.

28. The method of claim 27, wherein the reference sample is 2,2,4,6,6,-d5 testosterone.

29. The method of claim 28, wherein said reference sample is detected by ionizing said reference to produce one or more ions detectable by mass spectrometry having a mass/charge ratio selected from the group consisting of 294.1±0.5, 113.2±0.5, and 99.9±0.5.

30. The method of claim 29 wherein said ionizing comprises generating a precursor ion having a mass/charge ratio (m/z) of about 294.1±0.5;
isolating the precursor ion by mass spectroscopy; and
effecting a collision between the isolated precursor ion and an inert collision gas to produce one or more daughter ions detectable by mass spectrometry having a mass/charge ratio selected from the group consisting of 113.2±0.5, and 99.9±0.5.

31. The method of claim 19 further comprising determining the specificity of testosterone detection by calculating a ratio of the daughter ions for the sample and comparing that ratio with a daughter ion ratio for a purified sample of testosterone.

32. The method of claim 19 wherein detecting the presence or amount of the testosterone ion(s) by mass spectrometry involves combining the signal for ion 109.2±0.5 with the signal for ion 96.9±0.5 to obtained a summed daughter ion signal.

33. The method of claim 32 wherein the amount of testosterone is detected by comparing the summed daughter ion signal with a standard curve of summed daughter ion signals for known amounts of testosterone.

34. The method of claim 29 wherein detecting the presence or amount of the reference testosterone ion(s) by mass spectrometry involves combining the signal for ion 113.2±0.5, with the signal for ion and 99.9±0.5 to obtain a summed daughter ion signal.

35. A method for determining the presence or amount of testosterone in a test sample comprising,
(a) purifying testosterone from the test sample by turbulent flow chromatography;
(b) ionizing the purified testosterone by atmospheric pressure photoionization (APPI) to produce one or more testosterone ions detectable by a mass spectrometer having a mass/charge ratio selected from the group consisting of 289.1±0.5, 109.2±0.5, and 96.9±0.5; and
(c) detecting the presence or amount of the testosterone ion(s) by a mass spectrometer, wherein the presence or amount of the testosterone ion(s) is related to the presence or amount of testosterone in the test sample, wherein said ionizing and detecting utilize tandem mass spectrometry/time-of-flight (MS/MS/TOF) spectroscopy.

36. The method of claim 35 wherein the ionizing of step (b) comprises,
ionizing said testosterone from said sample to provide a precursor ion having a mass/charge ratio (m/z) of about 289.1±0.5;
isolating the precursor ion by mass spectroscopy; and
effecting a collision between the isolated precursor ion and an inert collision gas to produce one or more testosterone ions detectable by mass spectrometry having a mass/charge ratio selected from the group consisting of 109.2±0.5, and 96.9±0.5.

37. The method of claim 35, wherein the purifying step comprises:
(i) applying the sample to a high turbulence liquid chromatography (HTLC) extraction column;
(ii) washing the HTLC extraction column under conditions whereby testosterone is retained by the column;
(iii) eluting retained testosterone from the HTLC extraction column;
(iv) applying the retained material to an analytical column; and
(v) eluting purified testosterone from the analytical column.

38. The method of claim 37, wherein steps (i)-(v) are performed in an in-line automated fashion.

39. The method of claim 37, wherein steps (a) and (b) are performed in an in-line automated fashion with steps (i)-(v).

40. The method of claim 35 wherein the test sample is obtained from a human.

41. The method of claim 35 wherein the test sample is blood, serum, plasma, or urine.

42. The method of claim 41 wherein the test sample is deproteinated prior to the ionization step.

43. The method of claim 35 wherein the presence or amount of the testosterone ion is related to the presence or amount of testosterone in the test sample by comparison to a reference sample.

44. The method of claim 43, wherein the reference sample is 2,2,4,6,6,-d5 testosterone.

45. The method of claim 44, wherein said reference sample is detected by ionizing said reference to produce one or more ions detectable by mass spectrometry having a mass/charge ratio selected from the group consisting of 294.1±0.5, 113.2±0.5, and 99.9±0.5.

46. The method of claim 45 wherein said ionizing comprises generating a precursor ion having a mass/charge ratio (m/z) of about 294.1±0.5;
isolating the precursor ion by mass spectroscopy; and
effecting a collision between the isolated precursor ion and an inert collision gas to produce one or more daughter ions detectable by mass spectrometry having a mass/charge ratio selected from the group consisting of 113.2±0.5, and 99.9±0.5.

47. The method of claim 45 further comprising determining the specificity of testosterone detection by calculating a ratio of the daughter ions for the sample and comparing that ratio with a daughter ion ratio for a purified sample of testosterone.

48. The method of claim 45 wherein detecting the presence or amount of the testosterone ion(s) by mass spectrometry involves combining the signal for ion 109.2±0.5 with the signal for ion 96.9±0.5 to obtained a summed daughter ion signal.

49. The method of claim 48 wherein the amount of testosterone is detected by comparing the summed daughter ion signal with a standard curve of summed daughter ion signals for known amounts of testosterone.

50. The method of claim 45 wherein detecting the presence or amount of the reference testosterone ion(s) by mass spectrometry involves combining the signal for ion 113.2±0.5, with the signal for ion and 99.9±0.5 to obtain a summed daughter ion signal.

* * * * *